US007141403B2

(12) United States Patent
Outtrup et al.

(10) Patent No.: US 7,141,403 B2
(45) Date of Patent: Nov. 28, 2006

(54) ENDO-BETA-1,4-GLUCANASES

(75) Inventors: Helle Outtrup, Vaerlose (DK); Martin Schulein, deceased, late of Copenhagen (DK); Torben Henriksen, legal representative, Copenhagen (DK); Mads Eskelund Bjornvad, Frederiksberg (DK); Keith Gibson, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 11/044,363

(22) Filed: Jan. 26, 2005

(65) Prior Publication Data

US 2005/0215450 A1 Sep. 29, 2005

Related U.S. Application Data

(62) Division of application No. 10/479,446, filed as application No. PCT/DK02/00381 on Jun. 6, 2002, now Pat. No. 7,041,488.

(60) Provisional application No. 60/302,446, filed on Jun. 29, 2001.

(30) Foreign Application Priority Data

Jun. 6, 2001 (DK) ............................... 2001 00879

(51) Int. Cl.

| | |
|---|---|
| *C12N 9/24* | (2006.01) |
| *C12N 9/42* | (2006.01) |
| *C12N 15/74* | (2006.01) |
| *C12P 19/04* | (2006.01) |
| *C07H 21/04* | (2006.01) |

(52) U.S. Cl. ................... 435/209; 435/200; 435/252.3; 435/320.1; 435/69.1; 536/23.2

(58) Field of Classification Search ................ 435/200, 435/252.3, 471, 6, 320.1; 536/23.2
See application file for complete search history.

(56) References Cited

FOREIGN PATENT DOCUMENTS

| | | |
|---|---|---|
| EP | 4358796 | 6/1994 |
| EP | 307564 | 2/1996 |
| GB | 1368599 | 10/1974 |
| WO | WO 91/10732 | 7/1991 |
| WO | WO 91/17243 | 11/1991 |
| WO | WO 91/17244 | 11/1991 |
| WO | WO 95/24471 | 9/1995 |
| WO | WO 00/73428 | 12/2000 |
| WO | WO 02/20726 | 3/2002 |

OTHER PUBLICATIONS

Hakamada et al., Bioscience Biotechnology Biochem., Part 64, vol. 11, pp. 2281-2289 (2000).
Sumitomo et al., Bioscience Biotechnology Biochem., Part 56, vol. 6, pp. 872-877 (1992).
Fukumori et al., Journal of General Microbiology, vol. 132, pp. 2329-2335 (1986).
Miyatake et al., Database SWALL accession No. Q45554, "A Gene Encoding Endo-1,4-Beta-Glucanase from *Bacillus* sp. 22-28" (1996).
Ozaki et al., Journal of General Microbiology, vol. 136, pp. 1327-1334 (1990).
Fukumori et al., Gene, vol. 76, pp. 289-298 (1989).
M. K. Bhat., Biotechnology Advances, vol. 18, pp. 355-383 (2000).
Bernard Henrissat., Biochem., vol. 280, pp. 309-316 (1991).
Henrissat et al., Biochem., vol. 293, pp. 781-788 (1993).
Gilbert et al., Journal of Microbiology, vol. 139, pp. 187-194 (1993).
Patent Abstracts of Japan, Japanese Patent Office, JP 2000210081.

*Primary Examiner*—Kathleen M. Kerr
*Assistant Examiner*—Kagnew Gebreyesus
(74) *Attorney, Agent, or Firm*—Elias J. Lambiris

(57) ABSTRACT

The present invention relates to an enzyme exhibiting endo-beta-1,4-glucanase activity (EC 3.2.1.4), which is a) a polypeptide encoded by the DNA sequence of positions 1 to 2322 of SEQ ID NO: 1; b) a polypeptide produced by culturing a cell comprising the sequence of SEQ ID NO: 1 under conditions wherein the DNA sequence is expressed; c) an endo-beta-1,4-glucanase enzyme having a sequence of at least 97% identity to the amino acid sequence of position 1 to position 773 of SEQ ID NO: 2; and fragments thereof exhibiting endo-beta-1,4-glucanase activity, and d) a polypeptide having endo-beta-1,4-glucanase activity that is encoded by a polynucleotide that hybridizes with the nucleotide sequence shown in positions 1–2322 of SEQ ID NO: 1, is useful for detergent and textile applications.

25 Claims, No Drawings

SEQUENCE LISTING

```
<160> NUMBER OF SEQ ID NOS: 11

<210> SEQ ID NO 1
<211> LENGTH: 2322
<212> TYPE: DNA
<213> ORGANISM: Bacillus sp.
<220> FEATURE:
<221> NAME/KEY: CDS
<222> LOCATION: (1)..(2322)

<400> SEQUENCE: 1

gca gaa gga aac act cgt gaa gac aat ttt aaa cat tta tta ggt aat       48
Ala Glu Gly Asn Thr Arg Glu Asp Asn Phe Lys His Leu Leu Gly Asn
1               5                   10                  15

gac aat gtt aaa cgc cct tct gag gct ggc gca tta caa tta caa gaa       96
Asp Asn Val Lys Arg Pro Ser Glu Ala Gly Ala Leu Gln Leu Gln Glu
            20                  25                  30

gtc gat gga caa atg aca tta gta gat caa cat gga gaa aaa att caa      144
Val Asp Gly Gln Met Thr Leu Val Asp Gln His Gly Glu Lys Ile Gln
        35                  40                  45

tta cgt gga atg agt aca cac gga tta caa tgg ttt cct gar atc ttg      192
Leu Arg Gly Met Ser Thr His Gly Leu Gln Trp Phe Pro Glu Ile Leu
    50                  55                  60

aat gat aac gca tac aaa gct ctt gct aac gat tgg gaa tca aat atg      240
Asn Asp Asn Ala Tyr Lys Ala Leu Ala Asn Asp Trp Glu Ser Asn Met
65                  70                  75                  80

att cgt cta gct atg tat gtc ggt gaa aat ggc tat gct tca aat cca      288
Ile Arg Leu Ala Met Tyr Val Gly Glu Asn Gly Tyr Ala Ser Asn Pro
                85                  90                  95

gag tta att aaa agc aga gtc att aaa gga ata gat ctt gct att gaa      336
Glu Leu Ile Lys Ser Arg Val Ile Lys Gly Ile Asp Leu Ala Ile Glu
            100                 105                 110
```

-continued

```
aat gac atg tat gtt att gtt gat tgg cat gta cat gca cct ggt gat      384
Asn Asp Met Tyr Val Ile Val Asp Trp His Val His Ala Pro Gly Asp
        115                 120                 125

cct aga gat ccc gtt tac gct gga gca gaa gat ttc ttt aga gat att      432
Pro Arg Asp Pro Val Tyr Ala Gly Ala Glu Asp Phe Phe Arg Asp Ile
    130                 135                 140

gca gca tta tat cct aac aat cca cac att att tat gag tta gcg aat      480
Ala Ala Leu Tyr Pro Asn Asn Pro His Ile Ile Tyr Glu Leu Ala Asn
145                 150                 155                 160

gag cca agt agt aac aat aat ggt gga gct ggg att cca aat aat gaa      528
Glu Pro Ser Ser Asn Asn Asn Gly Gly Ala Gly Ile Pro Asn Asn Glu
                165                 170                 175

gaa ggt tgg aat gcg gta aaa gaa tac gct gat cca att gta gaa atg      576
Glu Gly Trp Asn Ala Val Lys Glu Tyr Ala Asp Pro Ile Val Glu Met
            180                 185                 190

tta cgt gat agc ggg aac gca gat gac aat atc atc att gtg ggt agt      624
Leu Arg Asp Ser Gly Asn Ala Asp Asp Asn Ile Ile Ile Val Gly Ser
        195                 200                 205

cca aac tgg agt cag cgt cct gac tta gca gct gat aat cca att aat      672
Pro Asn Trp Ser Gln Arg Pro Asp Leu Ala Ala Asp Asn Pro Ile Asn
    210                 215                 220

gat cac cat aca atg tat act gtt cac ttc tac act ggt tca cat gct      720
Asp His His Thr Met Tyr Thr Val His Phe Tyr Thr Gly Ser His Ala
225                 230                 235                 240

gct tca act gag agc tat ccg cct gaa act cct aac tct gaa aga gga      768
Ala Ser Thr Glu Ser Tyr Pro Pro Glu Thr Pro Asn Ser Glu Arg Gly
                245                 250                 255

aac gta atg agt aac act cgt tat gcg tta gaa aac gga gta gcg gta      816
Asn Val Met Ser Asn Thr Arg Tyr Ala Leu Glu Asn Gly Val Ala Val
            260                 265                 270

ttt gcg aca gaa tgg gga aca agt caa gca aat gga gat ggt ggt cct      864
Phe Ala Thr Glu Trp Gly Thr Ser Gln Ala Asn Gly Asp Gly Gly Pro
        275                 280                 285

tat ttt gat gaa gca gat gta tgg att gag ttt tta aat gaa aac aac      912
Tyr Phe Asp Glu Ala Asp Val Trp Ile Glu Phe Leu Asn Glu Asn Asn
    290                 295                 300

att agt tgg gct aac tgg tct tta acg aat aaa aat gaa gtg tct ggt      960
Ile Ser Trp Ala Asn Trp Ser Leu Thr Asn Lys Asn Glu Val Ser Gly
305                 310                 315                 320

gca ttt aca cca ttc gag tta ggt aag tct aac gca acc aat ctt gac     1008
Ala Phe Thr Pro Phe Glu Leu Gly Lys Ser Asn Ala Thr Asn Leu Asp
                325                 330                 335

cca ggt cca gat cat gtg tgg gca cca gaa gag tta agt ctt tcg gga     1056
Pro Gly Pro Asp His Val Trp Ala Pro Glu Glu Leu Ser Leu Ser Gly
            340                 345                 350

gaa tat gta cgt gct cgt att aaa ggt gtg aac tat gag cca atc gac     1104
Glu Tyr Val Arg Ala Arg Ile Lys Gly Val Asn Tyr Glu Pro Ile Asp
        355                 360                 365

cgt aca aaa tac acg aaa gta ctt tgg gac ttt aat gat gga acg aag     1152
Arg Thr Lys Tyr Thr Lys Val Leu Trp Asp Phe Asn Asp Gly Thr Lys
    370                 375                 380

caa gga ttt gga gtg aat tcg gat tct cca aat aaa gaa ctt att gca     1200
Gln Gly Phe Gly Val Asn Ser Asp Ser Pro Asn Lys Glu Leu Ile Ala
385                 390                 395                 400

gtt gat aat gaa aac aac act ttg aaa gtt tcg gga tta gat gta agt     1248
Val Asp Asn Glu Asn Asn Thr Leu Lys Val Ser Gly Leu Asp Val Ser
                405                 410                 415

aac gat gtt tca gat ggc aac ttc tgg gct aat gct cgt ctt tct gcc     1296
Asn Asp Val Ser Asp Gly Asn Phe Trp Ala Asn Ala Arg Leu Ser Ala
            420                 425                 430
```

-continued

```
gac ggt tgg gga aaa agt gtt gat att tta ggt gct gag aag ctt aca      1344
Asp Gly Trp Gly Lys Ser Val Asp Ile Leu Gly Ala Glu Lys Leu Thr
        435                 440                 445

atg gat gtt att gtt gat gaa cca acg acg gta gct att gcg gcg att      1392
Met Asp Val Ile Val Asp Glu Pro Thr Thr Val Ala Ile Ala Ala Ile
    450                 455                 460

cca caa agt agt aaa agt gga tgg gca aat cca gag cgt gct gtt cga      1440
Pro Gln Ser Ser Lys Ser Gly Trp Ala Asn Pro Glu Arg Ala Val Arg
465                 470                 475                 480

gtg aac gcg gaa gat ttt gtt cag caa acg gac ggt aag tat aaa gct      1488
Val Asn Ala Glu Asp Phe Val Gln Gln Thr Asp Gly Lys Tyr Lys Ala
                485                 490                 495

gga tta aca att aca gga gaa gat gct cct aac cta aaa aat atc gct      1536
Gly Leu Thr Ile Thr Gly Glu Asp Ala Pro Asn Leu Lys Asn Ile Ala
            500                 505                 510

ttt cat gaa gaa gat aac aat atg aac aac atc att ctg ttc gtg gga      1584
Phe His Glu Glu Asp Asn Asn Met Asn Asn Ile Ile Leu Phe Val Gly
        515                 520                 525

act gat gca gct gac gtt att tac tta gat aac att aaa gta att gga      1632
Thr Asp Ala Ala Asp Val Ile Tyr Leu Asp Asn Ile Lys Val Ile Gly
    530                 535                 540

aca gaa gtt gaa att cca gtt gtt cat gat cca aaa gga gaa gct gtt      1680
Thr Glu Val Glu Ile Pro Val Val His Asp Pro Lys Gly Glu Ala Val
545                 550                 555                 560

ctt cct tct gtt ttt gaa gac ggt aca cgt caa ggt tgg gac tgg gct      1728
Leu Pro Ser Val Phe Glu Asp Gly Thr Arg Gln Gly Trp Asp Trp Ala
                565                 570                 575

gga gag tct ggt gtg aaa aca gct tta aca att gaa gaa gca aac ggt      1776
Gly Glu Ser Gly Val Lys Thr Ala Leu Thr Ile Glu Glu Ala Asn Gly
            580                 585                 590

tct aac gcg tta tca tgg gaa ttt gga tat cca gaa gta aaa cct agt      1824
Ser Asn Ala Leu Ser Trp Glu Phe Gly Tyr Pro Glu Val Lys Pro Ser
        595                 600                 605

gat aac tgg gca aca gct cca cgt tta gat ttc tgg aaa tct gac ttg      1872
Asp Asn Trp Ala Thr Ala Pro Arg Leu Asp Phe Trp Lys Ser Asp Leu
    610                 615                 620

gtt cgc ggt gag aat gat tat gta gct ttt gat ttc tat cta gat cca      1920
Val Arg Gly Glu Asn Asp Tyr Val Ala Phe Asp Phe Tyr Leu Asp Pro
625                 630                 635                 640

gtt cgt gca aca gaa ggc gca atg aat atc aat tta gta ttc cag cca      1968
Val Arg Ala Thr Glu Gly Ala Met Asn Ile Asn Leu Val Phe Gln Pro
                645                 650                 655

cct act aac ggg tat tgg gta caa gca cca aaa acg tat acg att aac      2016
Pro Thr Asn Gly Tyr Trp Val Gln Ala Pro Lys Thr Tyr Thr Ile Asn
            660                 665                 670

ttt gat gaa tta gag gaa gcg aat caa gta aat ggt tta tat cac tat      2064
Phe Asp Glu Leu Glu Glu Ala Asn Gln Val Asn Gly Leu Tyr His Tyr
        675                 680                 685

gaa gtg aaa att aac gta aga gat att aca aac att caa gat gac acg      2112
Glu Val Lys Ile Asn Val Arg Asp Ile Thr Asn Ile Gln Asp Asp Thr
    690                 695                 700

tta cta cgt aac atg atg atc att ttt gca gat gta gaa agt gac ttt      2160
Leu Leu Arg Asn Met Met Ile Ile Phe Ala Asp Val Glu Ser Asp Phe
705                 710                 715                 720

gca ggg aga gtc ttt gta gat aat gtt cgt ttt gag ggg gct gct act      2208
Ala Gly Arg Val Phe Val Asp Asn Val Arg Phe Glu Gly Ala Ala Thr
                725                 730                 735

act gag ccg gtt gaa cca gag cca gtt gat cct ggc gaa gag acg cca      2256
Thr Glu Pro Val Glu Pro Glu Pro Val Asp Pro Gly Glu Glu Thr Pro
```

-continued

```
            740                 745                 750

cct gtc gat gag aag gaa gcg aaa aaa gaa caa aaa gaa gca gag aaa      2304
Pro Val Asp Glu Lys Glu Ala Lys Lys Glu Gln Lys Glu Ala Glu Lys
        755                 760                 765

gaa gag aaa gaa gag taa                                              2322
Glu Glu Lys Glu Glu
    770


<210> SEQ ID NO 2
<211> LENGTH: 773
<212> TYPE: PRT
<213> ORGANISM: Bacillus sp.

<400> SEQUENCE: 2

Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Glu Asp Phe Phe Arg Asp Ile
    130                 135                 140

Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asn
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
    290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
```

-continued

```
                325                 330                 335

Pro Gly Pro Asp His Val Trp Ala Pro Glu Glu Leu Ser Leu Ser Gly
            340                 345                 350

Glu Tyr Val Arg Ala Arg Ile Lys Gly Val Asn Tyr Glu Pro Ile Asp
        355                 360                 365

Arg Thr Lys Tyr Thr Lys Val Leu Trp Asp Phe Asn Asp Gly Thr Lys
    370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
                405                 410                 415

Asn Asp Val Ser Asp Gly Asn Phe Trp Ala Asn Ala Arg Leu Ser Ala
            420                 425                 430

Asp Gly Trp Gly Lys Ser Val Asp Ile Leu Gly Ala Glu Lys Leu Thr
        435                 440                 445

Met Asp Val Ile Val Asp Glu Pro Thr Thr Val Ala Ile Ala Ala Ile
    450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
                485                 490                 495

Gly Leu Thr Ile Thr Gly Glu Asp Ala Pro Asn Leu Lys Asn Ile Ala
            500                 505                 510

Phe His Glu Glu Asp Asn Asn Met Asn Asn Ile Ile Leu Phe Val Gly
        515                 520                 525

Thr Asp Ala Ala Asp Val Ile Tyr Leu Asp Asn Ile Lys Val Ile Gly
    530                 535                 540

Thr Glu Val Glu Ile Pro Val Val His Asp Pro Lys Gly Glu Ala Val
545                 550                 555                 560

Leu Pro Ser Val Phe Glu Asp Gly Thr Arg Gln Gly Trp Asp Trp Ala
                565                 570                 575

Gly Glu Ser Gly Val Lys Thr Ala Leu Thr Ile Glu Glu Ala Asn Gly
            580                 585                 590

Ser Asn Ala Leu Ser Trp Glu Phe Gly Tyr Pro Glu Val Lys Pro Ser
        595                 600                 605

Asp Asn Trp Ala Thr Ala Pro Arg Leu Asp Phe Trp Lys Ser Asp Leu
    610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
        675                 680                 685

Glu Val Lys Ile Asn Val Arg Asp Ile Thr Asn Ile Gln Asp Asp Thr
    690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750
```

-continued

```
Pro Val Asp Glu Lys Glu Ala Lys Lys Glu Gln Lys Glu Ala Glu Lys
        755                 760                 765

Glu Glu Lys Glu Glu
    770
```

<210> SEQ ID NO 3
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(42)
<223> OTHER INFORMATION: PRIMER LWN5494

<400> SEQUENCE: 3
gtcgccgggg cggccgctat caattggtaa ctgtatctca gc 42

<210> SEQ ID NO 4
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(64)
<223> OTHER INFORMATION: Primer LWN5495

<400> SEQUENCE: 4
gtcgcccggg agctctgatc aggtaccaag cttgtcgacc tgcagaatga ggcagcaaga 60
agat 64

<210> SEQ ID NO 5
<211> LENGTH: 61
<212> TYPE: DNA
<213> ORGANISM: artificial
<220> FEATURE:
<223> OTHER INFORMATION: Primer
<220> FEATURE:
<221> NAME/KEY: misc_feature
<222> LOCATION: (1)..(61)
<223> OTHER INFORMATION: PRIMER LWN5938

<400> SEQUENCE: 5
gtcggcggcc gctgatcacg taccaagctt gtcgacctgc agaatgaggc agcaagaaga 60
t 61

<210> SEQ ID NO 6
<211> LENGTH: 35
<212> TYPE: DNA
<213> ORGANISM: artificial
<220> FEATURE:
<223> OTHER INFORMATION: Primer
<220> FEATURE:
<221> NAME/KEY: misc_feature
<222> LOCATION: (1)..(35)
<223> OTHER INFORMATION: PRIMER LWN5939

<400> SEQUENCE: 6
gtcggagctc tatcaattgg taactgtatc tcagc 35

<210> SEQ ID NO 7
<211> LENGTH: 35
<212> TYPE: DNA

-continued

```
<213> ORGANISM: artificial
<220> FEATURE:
<223> OTHER INFORMATION: Primer
<220> FEATURE:
<221> NAME/KEY: misc_feature
<222> LOCATION: (1)..(35)
<223> OTHER INFORMATION: PRIMER LWN7864

<400> SEQUENCE: 7

aacagctgat cacgactgat cttttagctt ggcac                                35


<210> SEQ ID NO 8
<211> LENGTH: 37
<212> TYPE: DNA
<213> ORGANISM: artificial
<220> FEATURE:
<223> OTHER INFORMATION: Primer
<220> FEATURE:
<221> NAME/KEY: misc_feature
<222> LOCATION: (1)..(37)
<223> OTHER INFORMATION: PRIMER LWN7901

<400> SEQUENCE: 8

aactgcagcc gcggcacatc ataatgggac aaatggg                              37


<210> SEQ ID NO 9
<211> LENGTH: 42
<212> TYPE: DNA
<213> ORGANISM: artificial
<220> FEATURE:
<223> OTHER INFORMATION: Primer
<220> FEATURE:
<221> NAME/KEY: misc_feature
<222> LOCATION: (1)..(42)
<223> OTHER INFORMATION: PRIMER 168684

<400> SEQUENCE: 9

cattctgcag ccgcggcagc agaaggaaac actcgtgaag ac                        42


<210> SEQ ID NO 10
<211> LENGTH: 44
<212> TYPE: DNA
<213> ORGANISM: artificial
<220> FEATURE:
<223> OTHER INFORMATION: Primer
<220> FEATURE:
<221> NAME/KEY: misc_feature
<222> LOCATION: (1)..(44)
<223> OTHER INFORMATION: PRIMER 168685

<400> SEQUENCE: 10

gcgttgagac gcgcggccgc ttactcttct ttctcttctt tctc                      44


<210> SEQ ID NO 11
<211> LENGTH: 7
<212> TYPE: PRT
<213> ORGANISM: Bacillus sp.
<220> FEATURE:
<221> NAME/KEY: MISC_FEATURE
<222> LOCATION: (1)..(7)
<223> OTHER INFORMATION: N-TERMINAL, WHERE X=A

<400> SEQUENCE: 11

Xaa Glu Gly Asn Thr Arg Glu
1               5
```

ENDO-BETA-1,4-GLUCANASES

CROSS-REFERENCE TO RELATED APPLICATIONS

This application is a divisional of U.S. application Ser. No. 10/479,446 filed Dec. 2, 2003, now U.S. Pat. No. 7,041,488, which is a National Phase Application of PCT/DK02/00381 filed Jun. 6, 2002, which claims priority or the benefit under 35 U.S.C. 119 of Danish Application No. PA 2001 00879 filed Jun. 6, 2001 and U.S. Provisional Application No. 60/302,446 filed Jun. 29, 2001, the contents of which are fully incorporated herein by reference.

BACKGROUND OF THE INVENTION

1. Field of the Invention

The present invention relates to an enzyme exhibiting endo-beta-1,4-glucanase activity which enzyme is endogenous to the strain *Bacillus* sp., DSM 12648, to an isolated polynucleotide molecule encoding such an endo-beta-1,4-glucanase, and use of the enzyme in the detergent, paper and pulp, oil drilling, oil extraction, wine and juice, food ingredients, animal feed or textile industries.

2. Description of Related Art

Cellulose is a polymer of glucose linked by beta-1,4-glucosidic bonds. Cellulose chains form numerous intra- and intermolecular hydrogen bonds, which result in the formation of insoluble cellulose micro-fibrils. Microbial hydrolysis of cellulose to glucose involves the following three major classes of cellulases: (i) endoglucanases (EC 3.2.1.4) which cleave beta-1,4-glucosidic links randomly throughout cellulose molecules, also called endo-beta-1,4-glucanases; (ii) cellobiohydrolases (EC 3.2.1.91) which digest cellulose from the non-reducing end, releasing cellobiose; and (iii) beta-glucosidases (EC 3.2.1.21) which hydrolyze cellobiose and low molecular-weight cellodextrins to release glucose.

Beta-1,4-glucosidic bonds are also present in other naturally occurring polymers, e.g. in the beta-glucans from plants such as barley and oats. In some cases, endoglucanases also provide hydrolysis of such non-cellulose polymers.

Cellulases are produced by many micro-organisms and are often present in multiple forms. Recognition of the economic significance of the enzymatic degradation of cellulose has promoted an extensive search for microbial cellulases, which can be used industrially. As a result, the enzymatic properties and the primary structures of a large number of cellulases have been investigated. On the basis of the results of a hydrophobic cluster analysis of the amino acid sequence of the catalytic domain, these cellulases have been placed into different families of glycosyl hydrolases; fungal and bacterial glycosyl hydrolases have been grouped into 35 families (Henrissat, B.: A classification of glycosyl hydrolases based on amino acid sequence similarities. Biochem. J. 280 (1991), 309–316. Henrissat, B., and Bairoch, A.: New families in the classification of glycosyl hydrolases based on amino acid sequence similarities. Biochem. J. 293 (1993), 781–788). Most cellulases consist of a cellulose-binding domain (CBD) and a catalytic domain (CAD) separated by a linker which may be rich in proline and hydroxy amino acid residues. Another classification of cellulases has been established on the basis of the similarity of their CBDs (Gilkes et al. (1991)) giving five families of glycosyl hydrolases (I–V).

Cellulases are synthesized by a large number of micro-organisms which include fungi, actinomycetes, myxobacteria and true bacteria but also by plants. Especially endo-beta-1,4-glucanases of a wide variety of specificities have been identified. Many bacterial endoglucanases have been described (Gilbert, H. J. and Hazlewood, G. P. (1993) J. Gen. Microbiol. 139:187–194. Henrissat, B., and Bairoch, A.: New families in the classification of glycosyl hydrolases based on amino acid sequence similarities. Biochem. J. 293 (1993), 781–788).

An important industrial use of cellulolytic enzymes is for treatment of paper pulp, e.g. for improving the drainage or for de-inking of recycled paper. Another important industrial use of cellulolytic enzymes is for treatment of cellulosic textile or fabrics, e.g. as ingredients in detergent compositions or fabric softener compositions, for bio-polishing of new fabric (garment finishing), and for obtaining a "stone-washed" look of cellulose-containing fabric, especially denim, and several methods for such treatment have been suggested, e.g. in GB-A-1 368 599, EP 307 564 and EP 435 876, WO 91/17243, WO 91/10732, WO 91/17244, WO 95/24471 and WO 95/26398. JP patent application no. 13049/1999 discloses a heat resistant alkaline cellulase derived from *Bacillus* sp. KSM-S237 (deposited as FERM-P-16067) suitable for detergents.

There is an ever existing need for providing novel cellulase enzymes or enzyme preparations which may be used for applications where cellulase, preferably an endo-beta-1,4-glucanase, activity (EC 3.2.1.4) is desirable.

The object of the present invention is to provide novel enzymes and enzyme compositions having substantial beta-1,4-glucanase activity under slightly acid to alkaline conditions and improved performance in paper pulp processing, textile treatment, laundry processes, extraction processes or in animal feed; preferably such novel well-performing endoglucanases are producible or produced by using recombinant techniques in high yields.

SUMMARY OF THE INVENTION

The inventors have found a novel enzyme having substantial endo-beta-1,4-glucanase activity (classified according to the Enzyme Nomenclature as EC 3.2.1.4), which enzyme is endogenous to a strain of *Bacillus* sp. AA349 (DSM 12648), and the inventors have succeeded in cloning and expressing a DNA sequence encoding such an enzyme. The endo-beta-1,4-glucanase of the invention has stability and activity properties that make it exceptionally well-suited for use in applications involving aqueous alkaline solutions that contain surfactants and/or bleaches. Such application conditions are very commonly found, both within household and industrial detergents, textile finishing treatments and in the manufacture or recycling of cellulosic pulps.

Because the beta-1,4-glucanase of the invention maintains its activity to an exceptional extent under such relevant application conditions it is contemplated that it will be more useful than other known enzymes, e.g., when used in detergents, for paper/pulp processing or for textile treatments.

Also it is noted that the beta-1,4-glucanase of the invention is not significantly inactivated by Fe(II) ions. A sensitivity of the enzyme activity to the presence of ferrous ions could place restrictions on the applicability of the enzyme, such as in processes taking place in metal containers.

Accordingly, in its first aspect the present invention relates to an enzyme exhibiting endo-beta-1,4-glucanase activity (EC 3.2.1.4) which is selected from one of (a) a polypeptide encoded by all or part of the DNA sequence of SEQ ID NO: 1; (b) a polypeptide produced by culturing a cell comprising the sequence of SEQ ID NO: 1 under conditions wherein the DNA sequence is expressed; (c) an endo-beta-1,4-glucanase enzyme having a sequence of at least 97%, preferably 98%, more preferred 98.5%, even more preferred 99% identity to (I) positions 1–773 of SEQ ID NO: 2, or a fragment thereof that has endoglucanase activity, (II) the amino acid sequence of positions 1 to about 340 of SEQ ID NO: 2 and (III) the amino acid sequence of positions 1 to from between about 540 and 773 of SEQ ID NO: 2, when identity is determined by GAP provided in the GCG program package using a GAP creation penalty of 3.0 and GAP extension penalty of 0.1; and (d) a polypeptide having endo-beta-1,4-glucanase activity that is encoded by a polynucleotide that hybridizes with the nucleotide sequence shown in positions 1–2322 of SEQ ID NO: 1 under hybridization conditions comprising 5×SSC at 45° C. and washing conditions comprising 2×SSC at 60° C. In a preferred embodiment such fragment is a polypeptide which consists of position 1 to position 663±50 amino acids, preferably position 1 to 663±25 amino acids.

In its second aspect the invention relates to an isolated polynucleotide molecule, preferably a DNA molecule, encoding the catalytically active domain of an enzyme exhibiting endo-beta-1,4-glucanase activity which molecule is selected from the group consisting of (a) polynucleotide molecules comprising a nucleotide sequence as shown in SEQ ID NO: 1 from nucleotide 1 to nucleotide 2322, (b) species homologs of (a); (c) polynucleotide molecules that encode a polypeptide that is at least 97%, preferably 98%, more preferred 98.5%, even more preferred 99% identical to the amino acid sequence of SEQ ID NO: 2 from amino acid residue 1 to amino acid residue 773, and (c) degenerate nucleotide sequences of (a) or (b); preferably a polynucleotide molecule capable of hybridizing to a denatured double-stranded DNA probe under medium stringency conditions, wherein the probe is selected from the group consisting of DNA probes comprising the sequence shown in positions 1–2322 of SEQ ID NO: 1 and DNA probes comprising a subsequence of positions 1–2322 of SEQ ID NO: 1 having a length of at least about 100 base pairs.

In its third, fourth and fifth aspect the invention provides an expression vector comprising a DNA segment which is, e.g., a polynucleotide molecule of the invention; a cell comprising the DNA segment or the expression vector; and a method of producing an enzyme exhibiting endoglucanase activity, which method comprises culturing the cell under conditions permitting the production of the enzyme, and recovering the enzyme from the culture.

In yet another aspect the invention provides an isolated enzyme exhibiting endo-beta-1,4-glucanase activity, characterized in (i) being free from homologous impurities and (ii) the enzyme is produced by the method described above.

In a preferred embodiment of the present invention, the endoglucanase exhibits activity at a pH in the range of 5–11, preferably with a pH optimum at 6–10.5, and at temperatures from 20 to 60° C.

The endoglucanase comprises a catalytically active domain belonging to family 5 of glycosyl hydrolases (this domain corresponds to about position 1 to about position 340 of SEQ ID NO: 2), and a cellulase binding domain (CBD) belonging to family 17 (this domain corresponds to about position 341 to about position 540 of SEQ ID NO: 2). The remainder of SEQ ID NO: 2 are domains of unknown function.

The endoglucanase of the invention is advantageous in a number of industrial applications, especially in detergent compositions due to improved anti-redeposition and detergency effects, and in the treatment of textile.

DETAILED DESCRIPTION OF THE INVENTION

The strain *Bacillus* sp. AA349, which has been isolated from a soil sample originating in Greece, was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on 25 Jan. 1999 under the deposition number DSM 12648.

The term “functional enzymatic properties” as used herein is intended to mean physical and chemical properties of a polypeptide exhibiting one or more catalytic activities. Examples of functional enzymatic properties are enzymatic activity, specific enzymatic activity, relative enzymatic activity to the maximum activity (measured as a function of either pH or temperature), stability (degradation of enzymatic activity over time), DSC melting temperature, N-terminal amino acid sequence, molecular weight (usually measured in SDS-PAGE), isoelectric point (pI).

In the present context the term “expression vector” denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term “recombinant expressed” or “recombinantly expressed” used herein in connection with expression of a polypeptide or protein is defined according to the standard definition in the art. Recombinant expression of a protein is generally performed by using an expression vector as described immediately above.

The term “isolated”, when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). The term “an isolated polynucleotide” may alternatively be termed “a cloned polynucleotide”.

When applied to a protein/polypeptide, the term “isolated” indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention), which originate from the homologous cell from which the polypeptide of the invention is originally obtained.

The term "obtained from" as used herein in connection with a specific microbial source, means that the polynucleotide and/or polypeptide is produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5'-ATGCACGGG-3' is complementary to 5'-CCCGTGCAT-3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

Polynucleotides:

Within preferred embodiments of the invention an isolated polynucleotide of the invention will hybridize to similar sized regions of SEQ ID NO: 1 or a sequence complementary thereto, under at least medium stringency conditions.

In particular, polynucleotides of the invention will hybridize to a denatured double-stranded DNA probe comprising either the full sequence encoding the catalytic domain of the enzyme which sequence is shown in positions 1–2322 of SEQ ID NO: 1 or any probe comprising a subsequence of SEQ ID NO: 1 having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. (1989) Molecular Cloning: A Laboratory Manual, Cold Spring Harbor Lab., Cold Spring Harbor, NY) for 10 min, and prehybridization of the filter in a solution of 5×SSC, 5×Denhardt's solution (Sambrook et al. 1989), 0.5% SDS and 100 micrograms/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×109 cpm/microgram) probe for 12 hours at about 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using an x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having endoglucanase activity of the invention are then identified and isolated by, for example, hybridization or PCR.

The present invention further provides counterpart polypeptides and polynucleotides from different bacterial strains (orthologs or paralogs). Of particular interest are endoglucanase polypeptides from gram-positive alkalophilic strains, including species of *Bacillus*.

Species homologues of a polypeptide with endoglucanase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA sequence of the invention encoding an polypeptide having endoglucanase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the endoglucanase cloned from B. sp., DSM 12648, expressed and purified as described in Materials and Methods and Examples 1 and 2, or by an activity test relating to a polypeptide having endoglucanase activity.

The endoglucanase encoding part of the DNA sequence shown in SEQ ID NO: 1 and/or an analogue DNA sequence of the invention may be cloned from a strain of the bacterial species *Bacillus* sp., preferably the strain DSM12648, producing the enzyme with endoglucanase activity, or another or related organism as described herein.

How to use a sequence of the invention to get other related sequences: The disclosed sequence information herein relating to a polynucleotide sequence encoding an endo-beta-1,4-glucanase of the invention can be used as a tool to identify other homologous endoglucanases. For instance, polymerase chain reaction (PCR) can be used to amplify sequences encoding other homologous endoglucanases from a variety of microbial sources, in particular of different *Bacillus* species.

Polypedtides:

The sequence of amino acids in position 1 to position 773 of SEQ ID NO: 2 is a mature endoglucanase sequence with a calculated molecular weight of 86 kDa. It is believed that positions 1 to about 340 of SEQ ID NO: 2 are the catalytically active domain of the of the present endoglucanase enzyme. It is also believed that positions from about 340 to about 540 are the cellulose binding domain of the present endoglucanase enzyme. The function of the remainder of the sequence, i.e., from about position 540 to position 773, is at present unknown.

The present invention provides an endoglucanase enzyme comprising (i) the amino acid sequence of position 1 to position 773 of SEQ ID NO: 2, or a fragment thereof that has endoglucanase activity.

A fragment of position 1 to position 773 of SEQ ID NO: 2 is a polypeptide, which have one or more amino acids deleted from the amino and/or carboxyl terminus of this amino acid sequence. In an embodiment the present invention provides an endoglucanase enzyme comprising (ii) the amino acid sequence of positions 1 to about 340 of SEQ ID NO: 2, since it is contemplated that such a mono-domain endoglucanase is also useful in the industrial applications described herein. In another embodiment the present invention provides an endoglucanase enzyme comprising (iii) the amino acid sequence of positions 1 to a position from between about 540 and 773 of SEQ ID NO: 2, since it is contemplated that such an endoglucanase comprising the catalytically active domain and the cellulose binding domain is also useful in the industrial applications described herein. In a preferred embodiment such fragment is a polypeptide which consists of position 1 to position 663±50 amino acids, preferably 1 to 663±25 amino acids.

The present invention also provides endoglucanase polypeptides that are substantially homologous to the polypeptide of (i), (ii), or (iii) above and species homologs (paralogs or orthologs) thereof. The term "substantially homologous" is used herein to denote polypeptides being at least 97%, preferred 98%, more preferred 98.5% identical, and most preferably 99% or more identical to the sequence shown in amino acids nos. 1–773 of SEQ ID NO: 2, or a fragment thereof that has endoglucanase activity, or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., EMBO J. 4:1075, 1985; Nilsson et al., Methods Enzymol. 198:3, 1991. See, in general Ford et al., Protein Expression and Purification 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a polypeptide of the invention having endoglucanase activity.

TABLE 1

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the endoglucanase polypeptides of the present invention can be identified according to procedures known in the art, such as site-directed mutagenesis or alanine-scanning mutagenesis (Cunningham and Wells, Science 244: 1081–1085, 1989). In the latter technique, single alanine mutations are introduced at every residue in the molecule, and the resultant mutant molecules are tested for biological activity (i.e., endoglucanase activity) to identify amino acid residues that are critical to the activity of the molecule. See also, Hilton et al., J. Biol. Chem. 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306–312, 1992; Smith et al., J. Mol. Biol. 224:899–904, 1992; Wlodaver et al., FEBS Lett. 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (Science 241:53–57, 1988), Bowie and Sauer (Proc. Natl. Acad. Sci. USA 86:2152–2156, 1989), WO 95/17413, or WO 95/22625. Briefly, these authors disclose methods for simultaneously randomizing two or more positions in a polypeptide, or recombination/shuffling of different mutations (WO 95/17413, WO 95/22625), followed by selecting for functional a polypeptide, and then sequencing the mutagenized polypeptides to determine the spectrum of allowable substitutions at each position. Other methods that can be used include phage display (e.g., Lowman et al., Biochem. 30:10832–10837, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to the polypeptides of (I), (II), or (III) above and retain the endoglucanase activity of the wild-type protein.

The endoglucanase enzyme of the invention may, in addition to the enzyme core comprising the catalytically active domain, i.e. positions 1 to about 340 of SEQ ID NO: 2, also comprise a cellulose binding domain (CBD), the cellulose binding domain and the catalytically active domain being operably linked. The cellulose binding domain (CBD) may exist as an integral part of the encoded enzyme as described above and in the appended SEQ ID NO: 2, or be a CBD from another origin, introduced into the endoglucanase thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases (endoglucanases), xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the endoglucanase and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of a polypeptide corresponding at least to the catalytically active domain encoded by the DNA sequence of the invention.

In a similar way, the cellulose binding domain corresponding to from about position 340 to about position 540 of SEQ ID NO: 2 can be used to form hybrids with endoglucanases from sources other than *Bacillus* sp. AA349 and with other proteins. Examples of endoglucanases from other sources replacing the endoglucanase of positions 1 to about 340 of SEQ ID NO: 2 include endoglucanases from: (a) *Bacillus lautus* for instance *Bacillus lautus* NCIMB 40250 disclosed in WO 91/10732, (b) *Humicola insolens* DSM1800 disclosed in WO 91/17243 (c) *Fusarium oxysporium* DSM2672 disclosed in WO 91/17243 and (d) *Bacillus* sp. AC13 NCIMB 40482 disclosed in EP 0651785.

Immunological Cross-reactivity

Polyclonal antibodies, especially mono-specific polyclonal antibodies, to be used in determining immunological cross-reactivity may be prepared by use of a purified cellulolytic enzyme. More specifically, antiserum against the endoglucanase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation ($(NH_4)_2$ $SO_4$), followed by dialysis and ion exchange chromatography, e.g. on DEAE-Sephadex. Immunochemical characterization of proteins may be done either by Ouchterlony double-diffusion analysis (O. Ouchterlony in: Handbook of Experimental Immunology (D. M. Weir, Ed.), Blackwell Scientific Publications, 1967, pp. 655–706), by rocket immunoelectrophoresis or by crossed immunoelectrophoresis (N. Axelsen et al. in: A Manual of Quantitative Immunoelectrophoresis, Blackwell Scientific Publications, 1973, Chapters 2, 3 and 4).

Microbial Sources

For the purpose of the present invention the term "obtained from" or "obtainable from" as used herein in connection with a specific source, means that the enzyme is produced or can be produced by the specific source, or by a cell in which a gene from the source have been inserted.

It is at present contemplated that the endoglucanase of the invention may be obtained from a gram-positive bacterium belonging to a strain of the genus *Bacillus*, in particular a strain of *Bacillus* sp. AA349.

In a preferred embodiment, the endoglucanase of the invention is obtained from the strain *Bacillus* sp. AA349, DSM 12648. It is at present contemplated that a DNA sequence encoding an enzyme homologous to the enzyme of the invention may be obtained from other strains belonging to the genus *Bacillus*.

The strain *Bacillus* sp. AA349 from which the endoglucanase of the invention has been cloned has been deposited under the deposition number DSM 12648.

DNA Construct

In an aspect the present invention relates to a DNA construct for use in the integration of the polynucleotide of the invention into the host cell genome. The construct must comprise the polynucleotide of the invention flanked by two polynucleotide sequences, a first and a second DNA sequence, which flanking sequences each must comprise at least one subsequence of sufficient homology to a region on the host cell genome in order for efficient recombination to occur.

Recombinant Expression Vectors

A recombinant vector comprising a DNA construct encoding the enzyme of the invention may be any vector, which may conveniently be subjected to recombinant DNA procedures, and the choice of vector will often depend on the host cell into which it is to be introduced. Thus, the vector may be an autonomously replicating vector, i.e. a vector, which exists as an extra-chromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence, which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al. (1989) Molecular Cloning: A Laboratory Manual, Cold Spring Harbor Lab., Cold Spring Harbor, N.Y.).

Host Cells

The cloned DNA molecule introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the cloned DNA molecule or the recombinant vector of the invention is introduced may be any cell which is capable of producing the desired enzyme and includes bacteria, yeast, fungi and higher eukaryotic cells.

Examples of bacterial host cells which on cultivation are capable of producing the enzyme of the invention may be a gram-positive bacteria such as a strain of *Bacillus*, in particular *Bacillus alkalophilus, Bacillus amyloliquefaciens, Bacillus brevis, Bacillus lautus, Bacillus lentus, Bacillus licheniformis, Bacillus circulans, Bacillus coagulans, Bacillus megatherium, Bacillus stearothermophilus, Bacillus subtilis* and *Bacillus thuringiensis*, a strain of *Lactobacillus*, a strain of *Streptococcus*, a strain of *Streptomyces*, in particular *Streptomyces lividans* and *Streptomyces murinus*, or a strain of *Pseudomonas*, preferably a strain of *Pseudomonas fluorescens* or *Pseudomonas mendocina*, or the host cell may be a gram-negative bacteria such as a strain of *Escherichia coli*.

The transformation of the bacteria may be effected by protoplast transformation, electroporation, conjugation, or by using competent cells in a manner known per se (cf. e.g. Sambrook et al. (1989) Molecular Cloning: A Laboratory Manual, Cold Spring Harbor Lab., Cold Spring Harbor, N.Y.).

When expressing the enzyme in a bacterium such as *Escherichia coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in a gram-positive bacterium such as a strain of *Bacillus* or a strain of *Streptomyces*, the enzyme may be retained in the cytoplasm, or may be directed to the extracellular medium by a bacterial secretion sequence.

Examples of a fungal host cell which on cultivation may be capable of producing the enzyme of the invention is e.g. a strain of *Aspergillus* or *Fusarium*, in particular *Aspergillus awamori, Aspergillus nidulans, Aspergillus niger, Aspergillus oryzae*, and *Fusarium oxysporum*, and a strain of *Trichoderma*, preferably *Trichoderma harzianum, Trichoderma reesei* and *Trichoderma viride.*

Fungal cells may be transformed by a process involving protoplast formation and transformation of the protoplasts followed by regeneration of the cell wall in a manner known per se. The use of a strain of *Aspergillus* as a host cell is described in EP 238,023 (Novozymes A/S), the contents of which are hereby incorporated by reference.

Examples of a host cell of yeast origin which on cultivation may be capable of producing the enzyme of the invention is e.g. a strain of *Hansenula* sp., a strain of *Kluyveromyces* sp., in particular *Kluyveromyces lactis* and *Kluyveromyces marcianus*, a strain of *Pichia* sp., a strain of *Saccharomyces*, in particular *Saccharomyces carlsbergensis, Saccharomyces* cerevisae, *Saccharomyces kluyveri* and *Saccharomyces uvarum*, a strain of *Schizosaccharomyces* sp., in particular *Schizosaccharomyces pombe*, and a strain of *Yarrowia* sp., in particular *Yarrowia lipolytica.*

Examples of a host cell of plant origin which on cultivation may be capable of producing the enzyme of the invention is e.g. a plant cell of *Solanum tuberosum* or *Nicotiana tabacum.*

Method of Producing an Endoglucanase Enzyme

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

As defined herein, an isolated polypeptide (e.g. an enzyme) is a polypeptide which is essentially free of other polypeptides, e.g., at least about 20% pure, preferably at least about 40% pure, more preferably about 60% pure, even more preferably about 80% pure, most preferably about 90% pure, and even most preferably more than 95% pure, as determined by SDS-PAGE.

The term “isolated polypeptide” may alternatively be termed “purified polypeptide”.

When an expression vector comprising a DNA sequence encoding the enzyme is transformed into a heterologous host cell it is possible to enable heterologous recombinant production of the enzyme of the invention.

Thereby it is possible to make a highly purified or mono-component endo-beta-1,4-glucanase composition, characterized in being free from homologous impurities.

In this context, homologous impurities mean any impurities (e.g. other polypeptides than the enzyme of the invention) originating from the homologous cell from which the enzyme of the invention is originally obtained.

In the present invention the homologous host cell may be a strain of *Bacillus* sp. AA349.

The medium used to culture the transformed host cells may be any conventional medium suitable for growing the host cells in question. The expressed cellulolytic enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme Compositions

In a still further aspect, the present invention relates to an enzyme composition comprising an enzyme exhibiting endoglucanase activity as described above.

The enzyme composition of the invention may, in addition to the endoglucanase of the invention, comprise one or more other enzyme types, for instance hemicellulase such as xylanase and mannanase, other cellulase or endo-beta-1,4-glucanase components, chitinase, lipase, esterase, pectinase, cutinase, phytase, oxidoreductase (peroxidase, haloperoxidase, oxidase, laccase), protease, amylase, reductase, phenoloxidase, ligninase, pullulanase, pectate lyase, xyloglucanase, pectin acetyl esterase, polygalacturonase, rhamnogalacturonase, pectin lyase, pectin methylesterase, cellobiohydrolase, transglutaminase; or mixtures thereof.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Endoglucanases have potential uses in a lot of different industries and applications. Examples are given below of preferred uses of the enzyme composition of the invention. The dosage of the enzyme composition of the invention and other conditions under which the composition is used may be determined on the basis of methods known in the art.

The enzyme composition according to the invention may be useful for at least one of the following purposes.

Uses

Biomass Degradation

The enzyme or the enzyme composition according to the invention may be applied advantageously e.g. as follows:

- For debarking, i.e. pre-treatment with hydrolytic enzymes which may partly degrade the pectin-rich cambium layer prior to debarking in mechanical drums resulting in advantageous energy savings.
- For defibration (refining or beating), i.e. treatment of material containing cellulosic fibers with hydrolytic enzymes prior to the refining or beating which results in reduction of the energy consumption due to the hydrolyzing effect of the enzymes on the surfaces of the fibers.

For fibre modification, i.e. improvement of fibre properties where partial hydrolysis across the fibre wall is needed which requires deeper penetrating enzymes (e.g. in order to make coarse fibers more flexible).

For drainage: The drainability of papermaking pulps may be improved by treatment of the pulp with hydrolyzing enzymes. Use of the enzyme or enzyme composition of to the invention may be more effective, e.g. result in a higher degree of loosening bundles of strongly hydrated micro-fibrils in the fines fraction that limits the rate of drainage by blocking hollow spaces between the fibers and in the wire mesh of the paper machine.

The treatment of lignocellulosic pulp may, e.g., be performed as described in WO 93/08275, WO 91/02839 and WO 92/03608.

Laundry

The enzyme or enzyme composition of the invention may be useful in a detergent composition for household or industrial laundering of textiles and garments, and in a process for machine wash treatment of fabrics comprising treating the fabrics during one or more washing cycle of a machine washing process with a washing solution containing the enzyme or enzyme preparation of the invention.

Typically, the detergent composition used in the washing process comprises conventional ingredients such as surfactants (anionic, nonionic, zwitterionic, amphoteric), builders, bleaches (perborates, percarbonates or hydrogen peroxide) and other ingredients, e.g. as described in WO 97/01629 which is hereby incorporated by reference in its entirety.

The endo-beta-1,4-glucanase of the invention provides advantages such as improved stain removal and decreased soil redeposition. Certain stains, for example certain food stains, contain beta-glucans which make complete removal of the stain difficult to achieve. Also, the cellulosic fibres of the fabrics may possess, particularly in the “non-crystalline” and surface regions, beta-glucan polymers that are degraded by this enzyme. Hydrolysis of such beta-glucans, either in the stain or on the fabric, during the washing process decreases the binding of soils onto the fabrics.

Household laundry processes are carried out under a range of conditions. Commonly, the washing time is from 5 to 60 minutes and the washing temperature is in the range 15–60° C., most commonly from 20–40° C. The washing solution is normally neutral or alkaline, most commonly with pH 7–10.5. Bleaches are commonly used, particularly for laundry of white fabrics. These bleaches are commonly the peroxide bleaches, such as sodium perborate, sodium percarbonate or hydrogen peroxide.

Textile Applications

In another embodiment, the present invention relates to use of the endoglucanase of the invention in textile finishing processes, such as bio-polishing. Bio-polishing is a specific treatment of the yarn surface which improves fabric quality with respect to handle and appearance without loss of fabric wettability. The most important effects of bio-polishing can be characterized by less fuzz and pilling, increased gloss/luster, improved fabric handle, increased durable softness and altered water absorbency. Bio-polishing usually takes place in the wet processing during the manufacture of knitted and woven fabrics. Wet processing comprises such steps as e.g. desizing, scouring, bleaching, washing, dying/printing and finishing. During each of these steps, the fabric is more or less subjected to mechanical action. In general, after the textiles have been knitted or woven, the fabric proceeds to an optional desizing stage, followed by a scouring stage, etc. Desizing is the act of removing size from textiles. Prior to weaving on mechanical looms, warp yarns are often coated with size consisting of starch or starch derivatives in order to increase their tensile strength. After weaving, the size coating must be removed before further processing of the fabric in order to ensure a homogeneous and wash-proof result. In the scouring process impurities are removed from the fabric. The endoglucanase of the invention can advantageously be used in the scouring of cellulosic and cotton textiles, as well as bast fibers and may improve efficiency of removal of impurities.

One of the most commonly used methods for delivering durable press to cellulosic textiles is via finishing with cellulose crosslinking chemistry. Crosslinking immobilizes cellulose at a molecular level and substantially reduces shrinking and wrinkling of cellulosic garments. Treatment of durable press treated cellulosic textiles with the endoglucanase of the invention may result in a selective relaxation of stressed regions to minimize edge abrasion.

Additionally, the endoglucanase of the invention can be used to efficiently remove excess carboxymethyl cellulose-based print paste from textile and equipment used in the printing process.

It is known that in order to achieve the effects of bio-polishing, a combination of cellulolytic and mechanical action is required. It is also known that “super-softness” is achievable when the treatment with a cellulase is combined with a conventional treatment with softening agents. It is contemplated that use of the endoglucanase of the invention and of combinations of this enzyme with other enzymes for bio-polishing of cellulosics (natural and manufactured cellulosics, fabrics, garments, yarns, and fibers) is advantageous, e.g. a more thorough polishing can be achieved. It is believed that bio-polishing may be obtained by applying the method described e.g. in WO 93/20278. It is further contemplated that the endoglucanase of the invention can be applied to simultaneous or sequential textile wet processes, including different combinations of desizing, scouring, bleaching, bio-polishing, dyeing, and finishing.

Stone-washing

It is known that a “stone-washed” look (localized abrasion of the color) in dyed fabric, especially in denim fabric or jeans, can be provided either by washing the denim or jeans made from such fabric in the presence of pumice stones to provide the desired localized lightening of the colour of the fabric or by treating the fabric enzymatically, in particular with cellulytic enzymes. The treatment with an endoglucanase of the present invention, alone or in combination with other enzymes, may be carried out either alone such as disclosed in U.S. Pat. No. 4,832,864, together with a smaller amount of pumice than required in the traditional process, or together with perlite such as disclosed in WO 95/09225. Treatment of denim fabric with the endoglucanase of the invention may reduce backstaining compared to conventional methods.

MATERIALS & METHODS

Strains and Donor Organism

The *Bacillus* sp. DSM 12648 mentioned above comprises the endo-beta-1,4-glucanase encoding DNA sequence shown in SEQ ID NO: 1.

*B. subtilis* PL2306: This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315–4321) disrupted in the transcriptional unit of the known *Bacillus subtilis* cellulase gene, resulting in cellulase negative cells. The disruption was performed essentially as described in Eds. A. L. Sonenshein, J. A. Hoch and Richard Losick (1993) *Bacillus subtilis* and other Gram-Positive Bacteria, American Society for microbiology, p.618.

Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol. 121:296–304.

General Molecular Biology Methods

Unless otherwise stated all the DNA manipulations and transformations were performed using standard methods of molecular biology (Sambrook et al. (1989) Molecular Cloning: A Llaboratory Manual, Cold Spring Harbor Lab., Cold Spring Harbor, N.Y.; Ausubel, F. M. et al. (eds.) “Current protocols in Molecular Biology”. John Wiley and Sons, 1995; Harwood, C. R., and Cutting, S. M. (eds.) “Molecular Biological Methods for Bacillus”. John Wiley and Sons, 1990).

Enzymes for DNA manipulations were used according to the manufacturer’s instructions (e.g. restriction endonucleases, ligases etc. are obtainable from New England Biolabs, Inc.).

Plasmids pMOL944. This plasmid is a pUB110 derivative essentially containing elements making the plasmid propagate in *Bacillus subtilis*, kanamycin resistance gene and having a strong promoter and signal peptide cloned from the amyL gene of *B.licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of ordinary genetic engineering and is briefly described in the following.

Construction of pMOL944:

The pUB110 plasmid (McKenzie, T. et al., 1986, Plasmid 15:93–103) was digested with the unique restriction enzyme NciI. A PCR fragment amplified from the amyL promoter encoded on the plasmid pDN1981 (P. L. Jørgensen et al., 1990, Gene, 96, pp. 37–41) was digested with NciI and inserted in the NciI digested pUB110 to give the plasmid pSJ2624.

The two PCR primers used have the following sequences:

```
#LWN5494                                    (SEQ ID NO: 3)
5'-GTCGCCGGGGCGGCCGCTATCAATTGGTAACTGTATCTCAGC -3'

#LWN5495                                    (SEQ ID NO: 4)
5'-GTCGCCCGGGAGCTCTGATCAGGTACCAAGCTTGTCGACCTGCAGAA
TGAGGCAGCAAGAAGAT -3'
```

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

```
#LWN5938
                                            (SEQ ID NO: 5)
5'-GTCGGCGGCCGCTGATCACGTACCAAGCTTGTCGACCTGCAGAATGA
GGCAGCAAGAAGAT -3'

#LWN5939
                                            (SEQ ID NO: 6)
5'-GTCGGAGCTCTATCAATTGGTAACTGTATCTCAGC -3'
```

The plasmid pSJ2670 was digested with the restriction enzymes PstI and BclI and a PCR fragment amplified from a cloned DNA sequence encoding the alkaline amylase SP722 (WO 95/26397-A1) was digested with PstI and BclI and inserted to give the plasmid pMOL944. The two primers used for PCR amplification have the following sequence:

```
#LWN7864
                                            (SEQ ID NO: 7)
5'-AACAGCTGATCACGACTGATCTTTTAGCTTGGCAC-3'

#LWN7901
                                            (SEQ ID NO: 8)
5'-AACTGCAGCCGCGGCACATCATAATGGGACAAATGGG-3'
```

The primer #LWN7901 inserts a SacII site in the plasmid.

Genomic DNA Preparation

The strain DSM 12648 was propagated in liquid medium 2×TY containing 1% carboxymethyl-cellulose +(0.1 M $Na_2CO_3$+0.1 M $NaHCO_3$ separately autoclaved and added aseptically after cooling to room temperature). After 16 hours of incubation at 30° C. and 300 rpm, the cells were harvested, and genomic DNA was isolated by the method described by Pitcher et al. [Pitcher, D. G., Saunders, N. A., Owen, R. J; Rapid extraction of bacterial genomic DNA with guanidium thiocyanate; Lett Appl Microbiol 1989, 8:151–156].

Media

TY (as described in Ausubel, F. M. et al. (eds.): “Current protocols in Molecular Biology”, John Wiley and Sons, 1995).

2×TY (as described in Ausubel, F. M. et al. (eds.): “Current protocols in Molecular Biology”, John Wiley and Sons, 1995).

LB agar (as described in Ausubel, F. M. et al. (eds.): “Current protocols in Molecular Biology”, John Wiley and Sons, 1995).

LBPG is LB agar supplemented with 0.5% Glucose and 0.05 M potassium phosphate, pH 7.0

AZCL-HE-cellulose is added to LBPG-agar to 0.5% AZCL- HE-cellulose is from Megazyme, Australia.

BPX media is described in EP 0 506 780 (WO 91/09129).

Cal 18-2 media is described in WO 00/75344).

Determination of Endo-beta-1,4-glucanase Activity

ECU Method

In the ECU method the ability of the enzyme sample to reduce the viscosity of a solution of carboxymethyl-cellulose (CMC) is determined, and the result is given in ECU. The reduction in viscosity is proportional to the endo-cellulase activity. Conditions: CMC type 7LFD from Hercules, pH 7.5 in 0.1 M phosphate buffer, CMC concentration 31.1 g per liter reaction at 40° C. for 30 minutes. A vibration viscosimeter such as MIVI 3000, Sofraser, France is used to measure the viscosity.

Cellazyme C Method

Cellazyme C is an endoglucanase assay substrate, supplied in tablet form by Megazyme International Ireland Ltd. Reference is made to Megazyme's pamphlet CZC 7/99 which states: "The substrate is prepared by dyeing and cross-linking HE-cellulose to produce a material which hydrates in water but is water insoluble. Hydrolysis by endo-beta-1,4-glucanase produces water-soluble dyed fragments, and the rate of release of these (increase in absorbance at 590 nm) can be related directly to enzyme activity."

The enzyme sample is added to 6 ml of a suitable buffer in a test tube, one Cellazyme C tablet is added and dispersed by shaking the tube, then the tube is placed in a water bath at 40° C. The contents are mixed by brief shaking after approximately 15, 30, 45 and 60 minutes. After 60 minutes the solution is filtered through Whatman GF/C filters, 9 cm diameter. The absorbance of the filtered solution is measured at 590 nm.

The following examples illustrate the invention.

EXAMPLE 1

Cloning and Expression of Endo-beta-1,4-glucanase Gene from *Bacillus* sp.

Sub-cloning and Expression of Mature Endoglucanase in *B. subtilis*.

The endoglucanase encoding DNA sequence of the invention was PCR amplified using the PCR primer set consisting of these two oligo-nucleotides:

```
#168684
                                      (SEQ ID NO: 9)
5'-CAT TCT GCA GCC GCG GCA GCA GAA GGA AAC ACT CGT
GAA GAC-3'

#168685
                                     (SEQ ID NO: 10)
5'-GCG TTG AGA CGC GCG GCC GCT TAC TCT TCT TTC TCT
TCT TTC TC-3'
```

Restriction sites SacII and NotI are underlined.

The oligonucleotides were used in a PCR reaction in HiFidelity™ PCR buffer (Boehringer Mannheim, Germany) supplemented with 200 micro-M of each dNTP, 2.6 units of HiFidelity™ Expand enzyme mix and 200 pmol of each primer. Chromosomal DNA isolated from *Bacillus* sp. DSM12648 as described above was used as template.

The PCR reaction was performed using a DNA thermal cycler (Landgraf, Germany). One incubation at 94° C. for 1 min followed by ten cycles of PCR performed using a cycle profile of denaturation at 94° C. for 15 sec, annealing at 60° C. for 60 sec, and extension at 72° C. for 120 sec, followed by twenty cycles of denaturation at 94° C. for 15 sec, 60° C. for 60 sec and 72° C. for 120 sec (at this elongation step 20 sec are added every cycle). Five microliter aliquots of the amplification product was analysed by electrophoresis in 0.7% agarose gels (NuSieve, FMC). The appearance of a DNA fragment size 2.4 kb indicated proper amplification of the gene segment.

Subcloning of PCR Fragment:

Forty five microliter aliquots of the PCR products generated as described above were purified using QIAquick PCR purification kit (Qiagen, USA) according to the manufacturer's instructions. The purified DNA was eluted in 50 microliters of 10 mM Tris-HCl, pH 8.5.

Five micrograms of pMOL944 and 25 microliters of the purified PCR fragment was digested with SacII and NotI, electrophoresed in 0.7% agarose gels (NuSieve, FMC), the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 microgram of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 micrograms/ml of kanamycin-agar plates. After 18 hours incubation at 37° C. colonies were seen on the plates. Several clones were analyzed by isolating plasmid DNA from overnight culture broths.

One such positive clone was re-streaked several times on agar plates as used above; this clone was called MB1181-7. The clone MB1181-7 was grown overnight in TY-10 micrograms/ml kanamycin at 37° C., and next day 1 ml of cells were used to isolate a plasmid from the cells using the Qiaprep Spin Plasmid Miniprep Kit #27106 according to the manufacturers recommendations for *B. subtilis* plasmid preparations. This DNA was sequenced and revealed a DNA sequence identical to the endoglucanase gene in SEQ ID NO: 1 bp 1–2322 encoding the mature endoglucanase. The derived protein sequence is represented in SEQ ID NO: 2.

EXAMPLE 2

Expression and Recovery of the Endoglucanase from *Bacillus* sp. DSM 12648

MB1181-7 obtained as described in Example 1 was grown in 15×200 ml Cal-18-2 media with 10 micrograms/ml of kanamycin, in 500 ml two-baffled shake flasks, for 4 days at 37° C. at 300 rpm, whereby about 2500 ml of culture broth was obtained. The culture fluid was flocculated by adding 50% $CaCl_2$ (10 ml per liter of culture broth) together with 11% sodium aluminate (10 ml per liter of culture broth), maintaining the pH between 7.0 and 7.5 by adding 20% formic acid. Cationic agent Superfloc C521 (25 ml of a 10% v/v dilution per liter of culture broth) and anionic agent Superfloc A130 (75 ml of a 0.1% w/v dilution in water per liter of culture broth) was added during agitation to complete the flocculation. The flocculated material was separated by centrifugation using a Sorval RC 3B centrifuge at 10000 rpm for 30 min at 6° C. The resulting supernatant contained the endoglucanase activity.

The supernatant was clarified using Whatman glass filters GF/D and C. Then ultra-filtration was used to concentrate and reduce the ionic strength of the solution. The ultra-filtration membrane was Filtron UF with a cut-off of 10 kDa. After ultra-filtration the solution had conductivity<3 mS/cm. The pH was adjusted to pH 8.0.

Anion-exchange chromatography on Q-Sepharose was then used for additional purification. The solution from ultra-filtration was applied to a 300 ml column containing Q-Sepharose (Pharmacia) equilibrated with a buffer of 25 mmol Tris pH 8.0. The endoglucanase bound to the Q-Sepharose, and was then eluted using a 0.5 M NaCl gradient. The fractions with high endoglucanase activity were pooled. The endoglucanase activity of the final pooled endoglucanase solution was approximately 1000 ECU per ml.

EXAMPLE 3

Characterization of the Endoglucanase of the Invention

A sample of the endoglucanase from Example 2 was applied to a size chromatography column, using a 100 ml Superdex 200 column equilibrated in 0.1 M sodium acetate buffer pH 6.0. The endoglucanase eluted as a single peak. This purified enzyme solution was used for additional characterization, as below.

The enzyme from size chromatography purification gave a single band in SDS-PAGE at a position corresponding to a molecular weight of approximately 70 to 80 kDa, estimated as 73 kDa. The isoelectric point of the purified endoglucanase was around 4.2.

The N-terminal sequence was determined. The result was:

```
XEGNTRE (SEQ ID NO: 11)
```

The X was the injection, and could be A as found in the sequence based on the DNA sequence. Thus this N-terminal sequence does agree with the N-terminal sequence of SEQ ID NO: 2.

The protein concentration was determined using a molar extinction coefficient of 145800 (based on the amino acid composition deduced from the sequence).

Rabbit polyclonal mono-specific serum was raised against the purified enzyme using conventional techniques. The serum formed a single precipitate in agarose gels with the endoglucanase of the invention.

EXAMPLE 4

Stability at 40° C. in Solution Containing a Detergent and Bleach

The stability of the endoglucanase from Example 2 was evaluated under the following conditions.

A solution of a powder detergent with bleach was prepared. The powder detergent was IEC-A detergent, supplied by wfk Testgewebe GmbH, D-41379, Germany. This is an IEC 60456 Washing Machine Reference Base Detergent, type A. The bleach was IEC 60456 sodium perborate tetrahydrate, type SPB, also supplied by wfk Testgewebe.

Concentrations:

| | |
|---|---|
| Powder detergent, IEC-A: | 4.0 g per liter |
| Sodium perborate tetrahydrate: | 1.0 g per liter |
| Sodium bicarbonate: | 0.5 g per liter |
| Water hardness: | 15° dH (by adding a solution of calcium chloride plus magnesium chloride) |
| Solution pH: | 10.0 |

5 ml aliquots of the detergent solution were transferred to test tubes, and these were pre-heated in a 40° C. water bath for 10 minutes.

A solution of the enzyme, with activity 2.4 ECU/ml was prepared by diluting the sample from Example 2 with water.

One hundred microliters of the enzyme dilution was added to each of the pre-heated test tubes, and mixed. The solutions were kept at 40° C. for the specified period, then cooled quickly in ice water, then stored frozen.

Reference samples were prepared by adding 0, 50, 100, 150 microliters of the same enzyme solution into 5 ml samples of the detergent solution at room temperature, then cooling and freezing.

The activity in the heat treated and reference samples was then determined. The solutions were thawed and then 1 ml pH 9.5 buffer (see below) was added, giving total volume 6 ml. The activity was assayed using the Cellazyme C tablet method, as described in Materials & Methods section above.

The pH 9.5 buffer was prepared by mixing a) and b) to give pH 9.5:

(a) 0.25 M phosphate buffer pH 7.0 (prepared from $NaH_2PO_4.H_20$ and NaOH), containing 5.0 g/l of Berol 537 (nonionic surfactant from Akzo Nobel)

(b) 0.25 M sodium carbonate, containing 5.0 g/l of Berol 537 (nonionic surfactant from Akzo Nobel)

The activities in the heated samples were expressed as % of the activity found in the non-heated standards. The results were as follows:

| Time at 40° C., minutes | % activity |
|---|---|
| 0 | 99 |
| 15 | 96 |
| 30 | 92 |
| 45 | 91 |
| 60 | 90 |

Only about 10% of the activity was lost after one hour at 40° C. in this bleach-containing detergent solution.

EXAMPLE 5

Stability at 50° C. in Alkaline Solution Containing Bleach

The stability of the endoglucanase obtained in Example 2 was evaluated under the following conditions.

A solution of sodium perborate bleach (sodium perborate, tetrahydrate, type SPB from wfk Testgewebe) was prepared. Concentrations:

| | |
|---|---|
| Sodium perborate, tetrahydrate: | 1.25 g per liter |
| Glycine buffer, pH 9: | 0.1 M |

Five ml aliquots of this solution were transferred to test tubes, and these were pre-heated in a 50° C. water bath for 10 minutes.

A solution of the enzyme, with activity 2.5 ECU/ml was prepared by diluting the sample from Example 2 with water.

One hundred microliters of the enzyme dilution was added to each of the pre-heated test tubes, and the solution was mixed. The solutions were kept at 50° C. for the specified period, then cooled in ice water, and then stored frozen.

Reference samples were prepared by adding 0, 50, 100, 150 microliters of the same enzyme solution into 5 ml samples of the bleach solution at room temperature, then cooling and freezing.

The activity of the heat treated and reference samples was determined, following the same procedure as in Example 4.

The activities in the heated samples were expressed as % of the activity found in the non-heated standards. The results were as follows:

| Time at 50° C., minutes | % activity |
|---|---|
| 0 | 101 |
| 15 | 76 |
| 30 | 69 |
| 45 | 53 |
| 60 | 44 |

Less than 50% of the activity was lost after 30 minutes at 50° C. in this alkaline bleach solution.

EXAMPLE 6

Test for Inhibition by Fe(II) Ions

Inactivation of the endoglucanase from Example 2 by Fe(II) ions was evaluated as follows.

A 1 mM solution of Fe(II) sulphate was prepared by dissolving $FeSO_4.7H_2O$ (Merck, p.a.) in 0.1 M glycine buffer, pH 9.

Two solutions of the enzyme, with activity calculated to be 2.6 ECU/ml, were prepared by dilution the sample from Example 2 with a) 0.1 M glycine buffer, and b) 0.1 M glycine buffer with 1 mM Fe(II). These two solutions were stirred for 30 minutes at about 25° C.

Samples of 0, 50, 100, 150 microliters from these two solutions were then diluted in 6 ml of buffer (5 ml water plus 1 ml of the pH 9.5 buffer described in Example 4) and the activity determined by the Cellazyme C tablet method.

There was no significant activity difference between the samples prepared in glycine buffer and the corresponding samples prepared in glycine buffer plus $FeSO_4.7H_2O$.

The enzyme is not inactivated by treatment with 1 mM Fe(II) ions.

EXAMPLE 7

Wash Performance Test

This test demonstrates the stain removal and anti-redeposition effects of the endoglucanase obtained in Example 2. Additionally this test demonstrates that the enzyme performance is essentially unchanged when sodium perborate bleach is included.

Cotton swatches are stained with beta-glucan (from barley) plus carbon black. Soiled swatches are washed together with clean swatches. After washing the swatches are rinsed and dried. The soil removal from the soiled switches and the soil redeposition onto the clean swatches is determined by reflectance measurements. The soil removal and soil redeposition after washing without or with addition of the endoglucanase are compared.

Swatches: Cut from 100% cotton fabric, type #2003 (Tanigashira, Osaka, Japan), pre-washed at 40° C. as a precaution to remove any water soluble contaminations, size 5×5 cm, weight approximately 0.3 g.

Washing equipment: Stirred beakers, beaker volume 250 ml, with temperature control by water bath heating. The equipment is a multi-beaker miniature agitator washer.

Detergent solution: Prepared by adding the following into deionised water.

Sodium carbonate, 0.5 g per liter

Sodium bicarbonate, 0.7 g per liter $Ca^{2+}/Mg^{2+}$, to give water hardness 12° dH Anionic surfactant, Surfac SDBS80 (sodium alkylbenzene sulphonate), 0.5 g per liter Nonionic surfactant, Berol 537 (Akzo Nobel), 1.0 g per liter Sodium perborate, type SPB from wfk Testgewebe, either 0 or 1.0 g per liter Solution pH is approximately 9.5.

Washing procedure: 100 ml detergent solution is added to each beaker. The water bath temperature is 40° C. The mechanical agitators are operated at approximately 125 rpm. The detergent solutions are pre-warmed for 10 minutes and then the endoglucanase and the swatches are added. In each case three soiled swatches (prepared as described below) and three clean swatches are added to each beaker. After washing for 30 minutes, the swatches are removed from the detergent solution, rinsed under running tap water for 5 minutes, spread flat on absorbent paper and allowed to dry.

Reflectance measurements: Made using a Macbeth 7000 Color Eye reflectance spectrophotometer. In the case of the soiled swatches, each swatch is measured once in the center of the soiled area, then the average value is calculated. In the case of the clean swatches, each swatch is measured once on each side, then the average value is calculated. The reflectance measurements are all made at 500 nm.

Soiled swatches: Soiled swatches are made using beta-glucan (from barley) and carbon black ("carbon for detergency tests" supplied by Sentaku Kagaku Kyokai, Tokyo, Japan). Dissolve about 0.67 g of beta-glucan in 100 ml tap water by stirring and warming to >50° C. Add 0.33 g carbon black. Blend with an UltraTurrax T25 blender, speed 4000 rpm for 2 minutes. Apply 250 microliters of the beta-glucan/carbon onto the center of each swatch. Allow to dry overnight at room temperature.

The swatches used in this example had an average reflectance value of 93.5 before soil application and 17.5 after soiling.

Endoglucanase addition: The endoglucanase from Example 2 was added to give an activity concentration of 0, 20 or 100 ECU per liter of detergent solution.

Results: Detergent without bleach (average of reflectance measurements after washing)

| Endoglucanase added | Soiled swatches | Clean swatches |
|---|---|---|
| 0 | 25.1 | 33.5 |
| 20 ECU per liter | 35.7 | 46.7 |
| 100 ECU per liter | 40.2 | 59.1 |

Results: Detergent with bleach (average of reflectance measurements after washing)

| Endoglucanase added | Soiled swatches | Clean swatches |
|---|---|---|
| 0 | 24.6 | 27.7 |
| 20 ECU per liter | 36.8 | 52.6 |
| 100 ECU per liter | 39.3 | 63.2 |

The endoglucanase increased the removal of soil from the fabric, as seen by the increased reflectance value of the stained swatches after washing with endoglucanase as compared to the result after washing without endoglucanase. The endoglucanase also decreases the soil redeposition, as seen by the increased reflectance value of the clean swatches after washing with endoglucanase. The improvements of soil removal and anti-redeposition provided by the endoglucanase are essentially unchanged by the addition of the bleach.

EXAMPLE 8

Wash Performance Test

Clean cotton fabric is washed together with soiled cotton fabric in a solution of a household detergent. The wash is carried out in a Terg-O-Tometer. During the wash, soil is released from the soiled fabric into the detergent liquor. This soil can then redeposit onto the clean cotton. After washing, the cotton fabrics are rinsed and dried, and then measured with a reflectance spectrophotometer in order to detect the degree of soil redeposition.

Detergent: Powder household detergent, Asian.

Detergent concentration: 0.67 g/l in water with hardness 4° dH.

1000 ml of detergent solution per T-O-T beaker.

Cotton fabric: Total of 33 g fabric per T-O-T beaker, comprising suitably sized pieces of:

white woven cotton, #2003 (Tanigashira, Osaka, Japan), total weight 11 g white cotton interlock, total weight 13 g soiled cotton fabric, type EMPA101 (EMPA, Switzerland), total weight 9 g.

Wash: Temperature 25° C., wash time 40 minutes, at 125 rpm. After washing the #2003 cotton is rinsed under running tap water for 10 minutes, then dried.

Reflectance measurements. The pieces of #2003 woven cotton are measured, on both sides, using a Macbeth 7000 reflectance spectrophotometer, 500 nm. The average result for measurements from each T-O-M beaker is calculated.

Enzyme addition: In this trial, the endoglucanase prepared as described in Example 2 was added to the detergent liquor before the start of the wash step.

Results:

| Endoglucanase added, ECU per liter | Reflectance of #2003, at 500 nm |
|---|---|
| 0 | 76.67 |
| 0 | 76.05 |
| 1 | 81.86 |
| 5 | 84.30 |
| 20 | 84.85 |
| 50 | 85.99 |

From the results it can be concluded that addition of the endoglucanase of the invention reduces the soil redeposition.

EXAMPLE 9

Activity of Endoglucanase as a Function of pH and of Temperature

The activity of the endoglucanase from Example 2 was measured at a range of solution pH values, using a reaction temperature of 40° C.

The enzyme was first diluted with water to give a solution with activity approximately 0.07 ECU/ml.

Seven hundred fifty microliters of CMC solution (Hercules, type 7LFD, concentration 2% w/w dissolved in water) and 1000 microliters of a buffer solution were mixed in test tubes and pre-heated to 40° C. The buffers used are described below. Then 250 microliters of the 0.07 ECU/ml enzyme solution was added and the mix was incubated at 40° C. for 20 minutes. Then 1000 microliters of PHBAH reagent, described below, was added and the tubes were heated in boiling water for 10 minutes. Finally the solutions were cooled in ice water and the absorbance at 410 nm was measured with a spectrophotometer. Blank absorbance values, determined by adding the PHBAH reagent before adding the enzyme solution, were subtracted.

The PHBAH reagent was prepared as follows: Dissolve 1.5 g hydroxybenzoic acid hydrazide and 5.0 g potassium sodium tartrate in 100 ml of 2% w/w sodium hydroxide in water.

The following buffers were used. In all cases buffer concentration was 0.1 M.

Acetate buffers, pH 4.0, 4.5, 5.0, 5.5.

MES buffers, pH 6.0 (MES is 2-[N-morpholino]ethane sulfonic acid)

MOPS buffers, pH 6.5, 7.0, 7.5 (MOPS is 3-[N-morpholino]propane sulfonic acid)

Barbiturate buffers, pH 8.0, 8.5

Glycine buffers, pH 9.0, 9.5, 10.0, 10.5

The absorbance at 410 nm (minus the blank value) is a measure of the activity of the enzyme.

The results were as follows:

| pH during incubation (measured) | Absorbance, 410 nm (blank subtracted) |
|---|---|
| 4.2 | 0.0 |
| 4.6 | 0.0 |
| 5.1 | 0.1 |
| 5.7 | 0.2 |
| 6.1 | 0.3 |
| 6.5 | 0.4 |
| 7.1 | 0.6 |
| 7.5 | 0.8 |
| 8.1 | 0.9 |
| 8.5 | 1.0 |
| 9.2 | 0.9 |
| 9.6 | 1.0 |
| 10.0 | 1.0 |
| 10.5 | 0.9 |

The results show that the enzyme has maximum activity at alkaline pH. The enzyme has about 90% or more of the maximum activity in the pH range from 8.1 to 10.5.

The activity of the endoglucanase from Example 2 was measured at a range of temperatures, using a reaction pH of 10.0.

The enzyme was first diluted with water to give a solution with activity approximately 0.07 ECU/ml.

Seven hundred fifty microliters of CMC solution (Hercules, type 7LFD, concentration 2% w/w dissolved in water) and 1000 microliters of a 0.1 M glycine buffer solution pH 10.0 were mixed in test tubes and pre-heated to the specified temperature. Then 250 microliters of the 0.07 ECU/ml enzyme solution was added and the mix was incubated for 20 minutes at the specified temperature. Then 1000 microliters of PHBAH reagent, described above, was added and the tubes were heated in boiling water for 10 minutes.

Finally the solutions were cooled in ice water and the absorbance at 410 nm was measured with a spectrophotometer. Blank absorbance values, determined by adding the PHBAH reagent before adding the enzyme solution, were subtracted.

The absorbance at 410 nm (minus the blank value) is a measure of the activity of the enzyme.

The results were as follows:

| Incubation temperature, ° C. | Absorbance, 410 nm (blank subtracted) |
|---|---|
| 20 | 0.26 |
| 30 | 0.52 |
| 40 | 0.78 |
| 50 | 0.82 |
| 60 | 0.23 |
| 70 | <0.05 |

The enzyme has high activity at temperatures from 20 to 60° C., highest at temperatures around 40–50° C.

EXAMPLE 10

Biopolishing Using the Endoglucanase of the Invention in a Continuous Apparatus The fabric used is Knitted Fabric 460 (Test Fabrics Inc.), which is 100% cotton bleached interlock. The fabric is cut into 20×30 cm pieces weighing about 12.5 g each. The weight of each swatch is determined after conditioning for at least 24 hours at 65±2% relative humidity and 21±2° C. (70±3° F.).

The endoglucanase of the invention obtained in Example 2 is formulated in 15 mM sodium phosphate. The test is made with variable enzyme concentrations and at different pH.

Swatches are contacted with enzyme solutions for less than 45 seconds and then padded through a pad, after which they are weighed and hung immediately in a Mathis steam range (Type PSA-HTF) (Werner Mathis USA Inc. Concord, N.C.). The percentage of solution on fabric (% wet pick-up) and ratio of endoglucanase activity to fabric is determined. Fabric swatches are treated at 90° C. and 100% relative humidity for 90 minutes. All swatches are then transferred and rinsed in de-ionized water for at least 5 minutes, after which they are air dried. Finally, the swatches are conditioned at 65±2% relative humidity and 21±2° C. (70±3° F.) temperature for at least 24 hours before evaluation.

Fabric strength is measured on Mullen Burst tester model C according to ASTM D3786-87: Standard Test Method for Hydraulic Bursting Strength of Knitted Goods and Nonwoven Fabrics-Diaphragm Bursting Strength Tester Method, and strength loss is determined. Pilling note is measured according to ASTM D 4970-89: Standard Test Method for Pilling Resistance and Other Related Surface Changes of Textiles Fabrics (Martindale Pressure Tester Method). After 500 revolutions, pilling on the fabric is evaluated visually against a standard scale 1 to 5, where 1 indicates very severe pilling and 5 indicates no pilling.

EXAMPLE 11

Biopolishing Using the Endoglucanase of the Invention in a Continuous Apparatus Biopolishing is carried out essentially as described in Example 10, except that the buffer consist of 9.53 g sodium tetraborate decahydrate dissolved in 2.5 I deionized water and is adjusted to pH 9.2.

Swatches are padded and treated as described in Example 10. The fabric wet pick-up is 94%. The fabric is treated for 90 min at pH 9.2, 90° C., and relative humidity 100%. The rinsing, drying, evaluating procedures are the same as in Example 10.

EXAMPLE 12

Combination Treatments

The following experiment is performed to evaluate the effect of the endoglucanase obtained in Example 2 in combined scouring and biopolishing.

The fabric used is Fabric 4600, which is an unscoured and unbleached 100% cotton fabric. Fabric preparation and buffer are the same as described in Example 11 above.

The bulk solution contains: (a) The endoglucanase of Example 2 in a buffer as described in Example 2 above, at a concentration of 6.12 CMCU/ml and 4.9 CMCU/g fabric; and (b) thermostable pectate lyase at a concentration of 1.93 mv-mol/ml/min. Swatches are padded and treated as described in Example 10. The fabric wet pick-up is 80%. Treatment conditions are pH 9.2, 90° C., relative humidity (RH) 100%, and treatment is for 90 min.

The rinsing, drying, evaluating procedures are the same as described in Example 10 above. Wetting speed is evaluated according to the Standard MTCC (American Association of Textile Chemists and Colorists) Test Method 79-1995 “Absorbency of Bleached Textiles”. A water drop from 1 cm high burette is allowed to fall to a taut surface of fabric specimen. The time for water disappearance on the fabric surface is recorded as wetting time.

EXAMPLE 13

Denim Abrasion

The following example illustrates the use of the endoglucanase of the invention obtained in Example 2 to treat denim jeans or other garments and to produce denim garments with a uniformly localized color variation (denim abrasion). Abrasion refers to the faded color of warp-dyed denim due to combined effects of cellulase treatment and mechanical action. The resulting effect is a fabric appearance similar to that of stone-washed denim achieved with pumice stones.

Wash trials are carried out under the following conditions:

Textile

Blue denim DAKOTA, 14½ oz, 100% cotton. The denim is cut and sewn into “legs” of approximately 37.5×100 cm (about 375 g each).

Enzymes

Amylase: AQUAZYM™ ULTRA 1200 L (from Novozymes A/S)

Endoglucanase of the invention.

Denim Abrasion Protocol

Equipment: Tonello G130 Washing/Dyeing/Stone washing machine (Tonello S.r.I., Via della Fisica, 1/3, Sarcedo (VI)—Italia).

Textile Load: 8 kg denim "legs"

Desizing Step: 0.2% AQUAZYM™ ULTRA (% by weight of fabric)

0.05% Tergitol 15-S-9 (% by weight of fabric)

10 min

75° C.

LR (liquor ratio) 10:1

Rinse Step: 3 min, 60° C., LR 15:1

Abrasion Step: 10 ECU/g denim endoglucanase 60 min

50° C.

LR 8:1

Inactivation Step: 2% Sodium Carbonate (% by weight of fabric)

80° C.

20 min

LR 10:1

Rinse Steps: 2×3 min, LR 15:1

Extraction Step: 5 min at 110 g's

Tumble-dry the denim samples. Condition the samples for 24 hours at 20° C., 65% relative humidity prior to evaluation.

Tests/Analysis

Denim Abrasion and Backstaining

Measure the reflectance of the denim samples to determine the level of abrasion and backstaining. Denim Abrasion is measured as average L* (higher L* corresponds to more abrasion), and Backstaining is measured as average b* (more negative b*, "bluer," corresponds to more backstaining) on a HunterLab Labscan XE Spectrophotometer (Hunter Associates Laboratory, Inc., Reston, Va. 20190 USA).

Visual Assessment of Denim Abrasion and Backstaining

Five persons skilled in the art of evaluating denim are asked to visually grade the denim legs and assign a ranking of 1 (low effect) to 5 (high effect).

Weight Loss

Weigh the samples before and after treatment to determine the weight loss.

Tear Strength

The tear strength of the denim samples is determined using an Elmendorf Tearing tester according to ASTM D 1424-83 "Standard Test Method for Tear Resistance of Woven Fabrics by Falling Pendulum (Elmendorf) Apparatus."

The invention claimed is:

1. An isolated polynucleotide molecule encoding a polypeptide having endo-beta-1,4-endoglucanase activity which has an amino acid sequence which is at least 99% identical to the amino acid sequence of amino acids 1 to 773 of SEQ ID NO: 2.

2. The isolated polynucleotide molecule of claim 1, wherein the polynucleotide is DNA.

3. The isolated polynucleotide molecule of claim 1, which encodes a polypeptide having endo-beta-1,4-endoglucanase activity which has an amino acid sequence of position 1 to position 773 of SEQ ID NO: 2.

4. The isolated polynucleotide molecule of claim 1, which has a the nucleic acid sequence of nucleotides 1 to 2322 of SEQ ID NO: 1.

5. The isolated polynucleotide molecule of claim 1, which is isolated or produced from a prokaryote.

6. The isolated polynucleotide molecule of claim 1, which is isolated or produced from a bacterium.

7. The isolated polynucleotide molecule of claim 1, which is isolated or produced from a gram positive bacterium.

8. The isolated polynucleotide molecule of claim 1, which is isolated or produced from *Bacillus.*

9. The isolated polynucleotide molecule of claim 1 which is isolated or produced from *Bacillus* sp., DSM 12848.

10. A polynucleotide construct comprising the polynucleotide molecule of claim 1.

11. An expression vector comprising the following operably linked elements: a transcription promoter; a polynucleotide molecule of claim 1, and a transcription terminator.

12. An isolated cell into which has been introduced an expression vector of claim 11, wherein said cell expresses the polypeptide encoded by the polynucleotide molecule.

13. The cell of claim 12, which is a *Bacillus* cell.

14. The cell of claim 12, which is *Bacillus subtilis* or *Bacillus lentus* cell.

15. The cell of claim 12, which is a *Bacillus licheniformis* cell.

16. The cell of claim 12, which is a *Pseudomonas* cell.

17. The cell of claim 12, which is a *Streptomyces* cell.

18. The cell of claim 12, which is a *Saccharomyces* cell.

19. A method of producing a polypeptide having endo-beta-1,4-glucanase activity, comprising (a) culturing a cell of claim 12 under conditions to express the polypeptide; and (b) recovering the polypeptide.

20. An isolated polynucleotide molecule encoding a polypeptide having endo-beta-1,4-endoglucanase activity which is a fragment of the amino acid sequence of amino acids 1 to 773 of SEQ ID NO: 2, wherein the fragment has an amino acid sequence selected from the group consisting of:

(a) a sequence comprising amino acids 1 to 340 of SEQ ID NO: 2;

(b) a sequence comprising amino acid 1 to the amino acid in the range of 540 to 773 of SEQ ID NO: 2; and (c) a sequence consisting of amino acid 1 to the amino acid in the range of 613 to 713.

21. The isolated polynucleotide molecule of claim 20, wherein the polynucleotide is DNA.

22. A polynucleotide construct comprising the polynucleotide molecule of claim 20.

23. An expression vector comprising the following operably linked elements: a transcription promoter; a polynucleotide molecule of claim 20, and a transcription terminator.

24. An isolated cell into which has been introduced an expression vector of claim 23, wherein said cell expresses the polypeptide encoded by the polynucleotide molecule.

25. A method of producing a polypeptide having endo-beta-1,4-glucanase activity, comprising (a) culturing a cell of claim 24 under conditions to express the polypeptide; and (b) recovering the polypeptide.

* * * * *